United States Patent
Lange et al.

(10) Patent No.: US 7,173,044 B2
(45) Date of Patent: Feb. 6, 2007

(54) IMIDAZOLINE DERIVATIVES HAVING $CB_1$-ANTAGONISTIC ACTIVITY

(75) Inventors: Josephus H. M. Lange, Weesp (NL); Cornelis G. Kruse, Weesp (NL); Herman H. Van Stuivenberg, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 0 days.

(21) Appl. No.: 11/058,168

(22) Filed: Feb. 16, 2005

(65) Prior Publication Data

US 2005/0187259 A1 Aug. 25, 2005
US 2006/0241152 A9 Oct. 26, 2006

Related U.S. Application Data

(60) Provisional application No. 60/545,484, filed on Feb. 19, 2004.

(51) Int. Cl.
  *C70D 401/04* (2006.01)
  *C07D 233/24* (2006.01)
  *A61K 31/4545* (2006.01)
  *A61K 31/444* (2006.01)
  *A61K 31/4178* (2006.01)

(52) U.S. Cl. ............ 514/326; 514/341; 514/397; 546/210; 546/274.1; 548/315

(58) Field of Classification Search ............ None
See application file for complete search history.

(56) References Cited

U.S. PATENT DOCUMENTS

| | | | |
|---|---|---|---|
| 5,952,535 A * | 9/1999 | King et al. | 585/475 |
| 6,960,601 B2 * | 11/2005 | Smith et al. | 514/326 |
| 2004/0122074 A1 * | 6/2004 | Dow et al. | 514/397 |
| 2004/0235854 A1 * | 11/2004 | Kruse et al. | 514/252.05 |

FOREIGN PATENT DOCUMENTS

| WO | WO 03/026647 A1 | 4/2003 |
|---|---|---|
| WO | WO 03/027076 A2 | 4/2003 |
| WO | WO 03/078413 A1 | 9/2003 |

OTHER PUBLICATIONS

Dyck et al., "Potent Imidazole and Triazole CB1 receptor Antagonists Related to SR141716,"Bioorganic & Medicinal Chemistry Letters, vol. 14, Iss. 5, pp. 1151-1154 (2004).*

Co-Pending U.S. National Stage Application to Josephus H.M. Lange et al., based on International Patent Application No. PCT/EP2005/050680, filed Aug. 15, 2006.

International Preliminary Report on Patentability for International Application No. PCT/EP/2005/050680 (International Publication No. WO 2005/080345), Examiner I. Scruton-Evans, Nov. 16, 2005.

Khanna et al, "Selective Cyclooxygenase-2 Inhibitors: Heteroaryl Modified 1,2-Diarylimidazoles Are Potent, Orally Active Antiinflammatory Agents," *J. Med. Chem*, 2000, 43, 3168-3185.

Lange et al., "Synthesis, Biological Properties, and Molecular Modeling Investigations of Novel 3,4-Diarylpyrazolines as Potent and Elective $CB_1$ Cannabinoid Receptor Antagonists," *J. Med. Chem.*, 204, 47, 627-643 (2003).

International Search Report for corresponding PCT application No. PCT/EP2005/050680.

* cited by examiner

*Primary Examiner*—Joseph K. McKane
*Assistant Examiner*—Andrew B. Freistein
(74) *Attorney, Agent, or Firm*—Finnegan, Henderson, Farabow, Garrett & Dunner, L.L.P.

(57) ABSTRACT

The present invention relates to 1,2,4-tri-substituted imidazoline derivatives, to methods for the preparation of these compounds, to novel intermediates useful for the synthesis of said imidazoline derivatives, to methods for the preparation of these intermediates, to pharmaceutical compositions containing one or more of these imidazoline derivatives as active ingredient, as well as to the use of these pharmaceutical compositions for the treatment of psychiatric and neurological disorders. The compounds have the general formula (I)

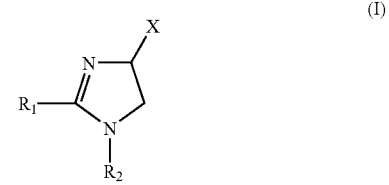

wherein the symbols have the meanings given in the specification.

7 Claims, No Drawings

IMIDAZOLINE DERIVATIVES HAVING CB₁-ANTAGONISTIC ACTIVITY

CROSS REFERENCE TO RELATED APPLICATION

This application claims the benefit of U.S. Provisional Application No. 60/545,484, filed Feb. 19, 2004, the content of which is incorporated herein by reference.

The present invention relates to 1,2,4-tri-substituted imidazoline derivatives as $CB_1$ antagonists, to methods for the preparation of these compounds and to novel intermediates useful for the synthesis of said imidazoline derivatives. The invention also relates to the use of a compound disclosed herein for the manufacture of a medicament giving a beneficial effect. A beneficial effect is disclosed herein or apparent to a person skilled in the art from the specification and general knowledge in the art. The invention also relates to the use of a compound of the invention for the manufacture of a medicament for treating or preventing a disease or condition. More particularly, the invention relates to a new use for the treatment of a disease or condition disclosed herein or apparent to a person skilled in the art from the specification and general knowledge in the art. In embodiments of the invention specific compounds disclosed herein are used for the manufacture of a medicament useful in the treatment of disorders in which cannabinoid receptors are involved, or that can be treated via manipulation of those receptors.

Multisubstituted imidazoline derivatives are known from WO 03/101954 and WO 03/101969. The compounds described therein, are potent inhibitors of transcription factor NF-KB, making them useful in the treatment of certain types of tumors. Said imidazoline derivatives also have potent activities as anti-inflammatory agents and antibiotics, leading to an additional array of indications in which they are likely to be of therapeutic interest, including inflammatory and infectious diseases. The compounds described in the abovementioned patent applications were not demonstrated to have any affinity for cannabinoid receptors, and therefore unlikely to be of therapeutic value in disorders in which these cannabinoid receptors are involved.

The goal of the present invention was to identify imidazoline derivatives with potent activity as cannabinoid-$CB_1$ receptor modulators, whilst maintaining essentially the physico-chemical properties that make some imidazoline derivatives useful therapeutic agents.

It has now surprisingly been found that potent antagonism or inverse agonism of cannabinoid-$CB_1$ receptors is present in the novel 4,5-dihydro-1H-imidazole derivatives of the formula (I):

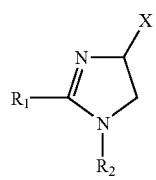

(I)

wherein:
$R_1$ and $R_2$ independently represent phenyl, thienyl or pyridyl which groups may be substituted with 1, 2 or 3 substituents Y, which can be the same or different, from the group branched or linear $C_{1-3}$-alkyl or $C_{1-3}$-alkoxy, phenyl, hydroxy, chloro, bromo, fluoro, iodo, trifluoromethyl, trifluoromethylthio, trifluoromethoxy, carboxyl, trifluoromethylsulfonyl, cyano, carbamoyl, sulfamoyl and acetyl, or $R_1$ and/or $R_2$ represent naphtyl,
X represents one of the subgroups (i) or (ii),

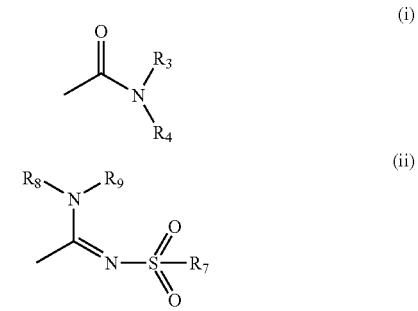

wherein:
$R_3$ represents a hydrogen atom or a branched or linear $C_{1-3}$ alkyl group,
$R_4$ represents a branched or linear $C_{1-8}$ alkyl or $C_{3-8}$-cycloalkyl-$C_{1-2}$-alkyl group, branched or linear $C_{1-8}$ alkoxy, $C_{3-8}$ cycloalkyl, $C_{5-10}$ bicycloalkyl, $C_{6-10}$ tricycloalkyl, which groups may contain one or more heteroatoms from the group (O, N, S) and which groups may be substituted with a hydroxy group, 1–3 methyl groups, an ethyl group or 1–3 fluoro atoms, or $R_4$ represents a phenyl, phenoxy, benzyl, phenethyl or phenylpropyl group, optionally substituted on their phenyl ring with 1–3 substituents Y, wherein Y has the abovementioned meaning, or $R_4$ represents a pyridyl or thienyl group, or $R_4$ represents a group $NR_5R_6$ wherein
$R_5$ and $R_6$—together with the nitrogen atom to which they are attached—form a saturated or unsaturated, monocyclic or bicyclic, heterocyclic group having 4 to 10 ring atoms, which heterocyclic group contains one or two heteroatoms from the group (O, N, S) and which heterocyclic group may be substituted with a branched or linear $C_{1-3}$ alkyl, phenyl, hydroxy or trifluoromethyl group or a fluoro atom, or
$R_3$ and $R_4$—together with the nitrogen atom to which they are attached—form a saturated or unsaturated, monocyclid or bicyclic, heterocyclic group having 4 to 10 ring atoms, which heterocyclic group contains one or two heteroatoms from the group (O, N, S) and which heterocyclic group may be substituted with a branched or linear $C_{1-3}$ alkyl, phenyl, amino, hydroxy or trifluoromethyl group or a fluoro atom,
$R_7$ represents a benzyl, phenyl, thienyl or pyridyl group, which groups may be substituted on their aromatic ring with 1, 2, 3 or 4 substituents Y, wherein Y has the meaning as indicated above, which can be the same or different, or $R_7$ represents $C_{1-8}$ branched or linear alkyl, $C_{3-8}$ alkenyl, $C_{3-8}$ alkenyl, $C_{3-10}$ cycloalkyl, $C_{5-10}$ bicycloalkyl, $C_{6-10}$ tricycloalkyl or $C_{5-8}$ cycloalkenyl or $R_7$ represents naphtyl or $R_7$ represents an amino group or $R_7$ represents a $C_{1-8}$ dialkylamino group, a $C_{1-8}$ monoalkylamino group or a saturated or unsaturated, monocyclic or bicyclic, heterocyclic group having 4 to 10 ring atoms, which heterocyclic group contains 1 or 2 nitrogen atoms and which heterocyclic group may contain 1 heteroatom from the group (O, S) and which heterocyclic group may be substituted with a branched or linear $C_{1-3}$ alkyl, phenyl, hydroxy or trifluoromethyl group or a fluoro atom, $R_8$ represents a hydrogen atom or a methyl group, $R_9$ represents a hydrogen atom or a methyl, ethyl or methoxy group and tautomers, stereoisomers, prodrugs and salts thereof.

At least one centre of chirality is present (at the $C_4$ position of the imidazoline moiety) in the compounds of the formula (I). The invention relates to racemates, mixtures of diastereomers as well as the individual stereoisomers of the compounds having formula (I). The invention also relates to the E isomer, Z isomer and E/Z mixtures of compounds having formula (I).

Prodrugs are therapeutic agents which are inactive per se but are transformed into one or more active metabolites. Prodrugs are bioreversible derivatives of drug molecules used to overcome some barriers to the utility of the parent drug molecule. These barriers include, but are not limited to, solubility, permeability, stability, presystemic metabolism and targeting limitations (Medicinal Chemistry: Principles and Practice, 1994, ISBN 0-85186-494-5, Ed.: F. D. King, p. 215; J. Stella, "Prodrugs as therapeutics", Expert Opin. Ther. Patents, 14(3), 277–280, 2004; P. Ettmayer et al., "Lessons learned from marketed and investigational prodrugs", J.Med.Chem., 47, 2393–2404, 2004). Pro-drugs, i.e. compounds which when administered to humans by any known route, are metabolised to compounds having formula (1), belong to the invention. In particular this relates to compounds with primary or secondary amino or hydroxy groups. Such compounds can be reacted with organic acids to yield compounds having formula (1) wherein an additional group is present which is easily removed after administration, for instance, but not limited to amidine, enamine, a Mannich base, a hydroxyl-methylene derivative, an O-(acyloxymethylene carbamate) derivative, carbamate, ester, amide or enaminone.

The invention particularly relates to compounds having formula (I)

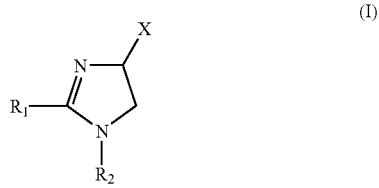

(I)

wherein:

$R_1$ and $R_2$ independently represent phenyl, which phenyl group may be substituted with 1, 2 or 3 substituents Y, which can be the same or different, from the group branched or linear $C_{1-3}$-alkyl or $C_{1-3}$-alkoxy, phenyl, hydroxy, chloro, bromo, fluoro, iodo, trifluoromethyl, trifluoromethylthio, trifluoromethoxy, carboxyl, trifluoromethylsulfonyl, cyano, carbamoyl, sulfamoyl and acetyl, or $R_1$ and/or $R_2$ represent naphtyl, thienyl or pyridyl, X represents one of the subgroups (i) or (ii),

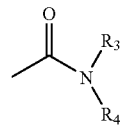

(i)

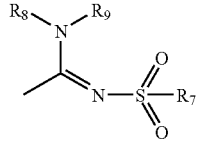

(ii)

wherein:

$R_3$ represents a hydrogen atom, $R_4$ represents a branched or linear $C_{1-8}$ alkyl, branched or linear $C_{1-8}$ alkoxy or $C_{3-8}$ cycloalkyl group, which groups may be substituted with a hydroxy group, 1–3 methyl groups, an ethyl group or 1–3 fluoro atoms, or $R_4$ represents a phenyl, phenoxy, pyridyl or thienyl group, or $R_4$ represents a group $NR_5R_6$ wherein $R_5$ and $R_6$—together with the nitrogen atom to which they are attached—form a saturated or unsaturated, monocyclic or bicyclic, heterocyclic group having 4 to 10 ring atoms, which heterocyclic group contains one or two heteroatoms from the group (O, N, S) or $R_3$ and $R_4$—together with the nitrogen atom to which they are attached—form a saturated or unsaturated, monocyclic or bicyclic, heterocyclic group having 4 to 10 ring atoms, which heterocyclic group contains one or two heteroatoms from the group (O, N, S) and which heterocyclic group may be substituted with a methyl, hydroxy or trifluoromethyl group or a fluoro atom, $R_7$ represents a phenyl group, which phenyl group may be substituted on its aromatic ring with 1, 2, 3 or 4 substituents Y, wherein Y has the meaning as indicated above, which can be the same or different, or $R_7$ represents $C_{1-8}$ branched or linear alkyl, $C_{3-10}$ cycloalkyl or $C_{5-10}$ bicycloalkyl, or $R_7$ represents naphtyl or $R_7$ represents a amino group or $R_7$ represents a $C_{1-8}$ dialkylamino group, a $C_{1-8}$ monoalkylamino group or a saturated or unsaturated, monocyclic or bicyclic, heterocyclic group having 4 to 10 ring atoms, which heterocyclic group contains 1 or 2 nitrogen atoms and which heterocyclic group may contain 1 heteroatom from the group (O, S) and which heterocyclic group may be substituted with a branched or linear $C_{1-3}$ alkyl or hydroxy group, $R_8$ represents a hydrogen atom, $R_9$ represents a hydrogen atom and tautomers, stereoisomers, prodrugs and salts thereof.

Due to the potent $CB_1$ antagonistic activity the compounds according to the invention are suitable for use in the treatment of psychiatric disorders such as psychosis, anxiety, depression, attention deficits, memory disorders, cognitive disorders, appetite disorders, obesity, in particular juvenile obesity and drug induced obesity, addiction, impulse control disorders, appetence, drug dependence and neurological disorders such as neurodegenerative disorders, dementia, dystonia, muscle spasticity, tremor, epilepsy, multiple sclerosis, traumatic brain injury, stroke, Parkinson's disease, Alzheimer's disease, epilepsy, Huntington's disease, Tourette's syndrome, cerebral ischaemia, cerebral apoplexy, craniocerebral trauma, stroke, spinal cord injury, neuroinflammatory disorders, plaque sclerosis, viral encephalitis, demyelinisation related disorders, as well as for the treatment of pain disorders, including neuropathic pain disorders, and other diseases involving cannabinoid neurotransmission, including the treatment of septic shock, glaucoma, cancer, diabetes, emesis, nausea, asthma, respiratory diseases, gastrointestinal disorders, gastric ulcers, diarrhoea, cardiovascular disorders, atherosclerosis, liver cirrhosis and sexual disorders.

The cannabinoid receptor modulating activity of the compounds of the invention makes them particularly useful in the treatment of obesity, juvenile obesity and drug induced obesity, when used in combination with lipase inhibitors. Specific examples of compounds which can be used in such combination preparations are (but not restricted to) the synthetic lipase inhibitor orlistat, lipase inhibitors isolated from micro organisms such as lipstatin (from *Streptomyces toxytricin*), ebelactone B (from *Streptomyces aburaviensis*), synthetic derivatives of these compounds, as well as extracts of plants known to possess lipase inhibitory activity, for instance extracts of *A. officinarum* or compounds isolated from such extracts like 3-methylethergalangin (from *A. officinarum*).

General Aspects of Syntheses

The synthesis of compounds having formula (I) wherein X represents subgroup (i) is outlined in Scheme 1. Intermediates having general formula (II) can be obtained according to methods known, see for example: I. K. Khanna et al., J. Med. Chem. 2000, 43, 3168–3185; I. K. Khanna et al., J. Med. Chem. 1997, 40, 1634–1647; WO 03/027076 or WO 03/040107. Intermediates having general formula (IV) can be obtained according to methods known, see for example: I. K. Khanna et al., J. Med. Chem. 2000, 43, 3168–3185.

Carboxamidine derivatives of general formula (II) can be reacted with 2-chloroacrylonitrile (III) to give a 4,5-dihydro-1H-imidazole derivative of general formula (IV). This reaction is preferably carried out in the presence of a base such as N,N-diisopropylethylamine. The obtained derivatives of general formula (IV) can be esterified with an alcohol $R_{10}$—OH to give a 4,5-dihydro-1H-imidazole derivative of general formula (V), wherein $R_{10}$ represents a branched or linear $C_{1-5}$ alkyl group or a benzyl group. This reaction is preferably carried out under acidic conditions. A compound of general formula (V) can react with an amine $R_3R_4NH$, preferably in the presence of trimethylaluminum ($Me_3Al$) to give a compound of formula (I), wherein X represents subgroup (i) and $R_3$ and $R_4$ have the meaning as given above on page 2. Additional information on trimethylaluminum $Al(CH_3)_3$ promoted amidation reactions of esters can be found in: J. I. Levin, E. Turos, S. M. Weinreb, *Synth Commun.* (1982), 12, 989–993.

Alternatively, a compound of general formula (V) can be hydrolysed to the corresponding carboxylic acid derivative of general formula (VI), wherein $R_{11}$ represents H or an earth alkali metal, in particular Li, Na or K. Alternatively, the compound of general formula (VI) can be reacted with a chlorinating agent such as thionylchloride to give the corresponding acid chloride. The compound of general formula (VI) can be reacted with an amine $R_3R_4NH$ to give a compound of formula (I), wherein X represents subgroup (i) and $R_3$ and $R_4$ have the meaning as given above on page 2, via activating and coupling methods such as formation of an active ester, or in the presence of a so-called coupling reagent, such as for example, DCC, HBTU, BOP (benzotriazol-1-yloxytris(dimethylamino)phosphonium hexafluorophosphate) and the like.

Additional information on activating and coupling methods of amines to carboxylic acids can be found in:

a) M. Bodanszky and A. Bodanszky: *The Practice of Peptide Synthesis*, Springer-Verlag, New York, 1994; ISBN: 0-387-57505-7;

b) K. Akaji et al., *Tetrahedron Lett.* (1994), 35, 3315–3318);

c) F. Albericio et al., *Tetrahedron Lett.* (1997), 38, 4853–4856).

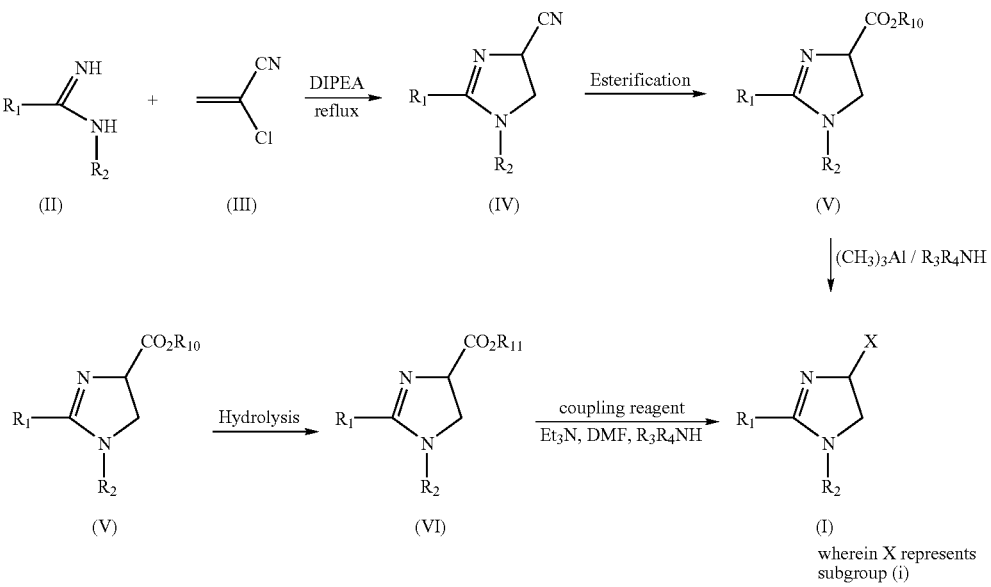

Scheme 1

The synthesis of compounds having formula (I) wherein X represents subgroup (ii) is outlined in Scheme 2.

An intermediate of general formula $R_7SO_2NH_2$ is either commercially available or can be prepared via standard synthetic methodology, for example from the corresponding compound $R_7SO_2Cl$ (see for example; McManus et al., J. Med. Chem. 1965, 8, 766). A compound of general formula (IV) can be reacted with a compound of general formula $R_7SO_2NH_2$ in the presence of a Lewis acid such as for example $AlMe_3$ in an inert organic solvent such as benzene to give a compound of general formula (I) wherein X represents subgroup (ii) and $R_1$, $R_2$ and $R_7$ have the meaning as given above on the pages 1–3 and wherein $R_8$ and $R_9$ represent a hydrogen atom. A compound of general formula (V) may be reacted with a compound of general formula $R_7SO_2NH_2$ to give a compound of general formula (VII). This reaction is preferably carried out in the presence of a strong non-nucleophilic base. A compound of general formula (VII) may be reacted with a chlorinating reagent in a chloroimidation reaction and subsequently treated with an amine $R_8R_9NH$ to give a compound of formula (I), wherein X represents subgroup (ii).

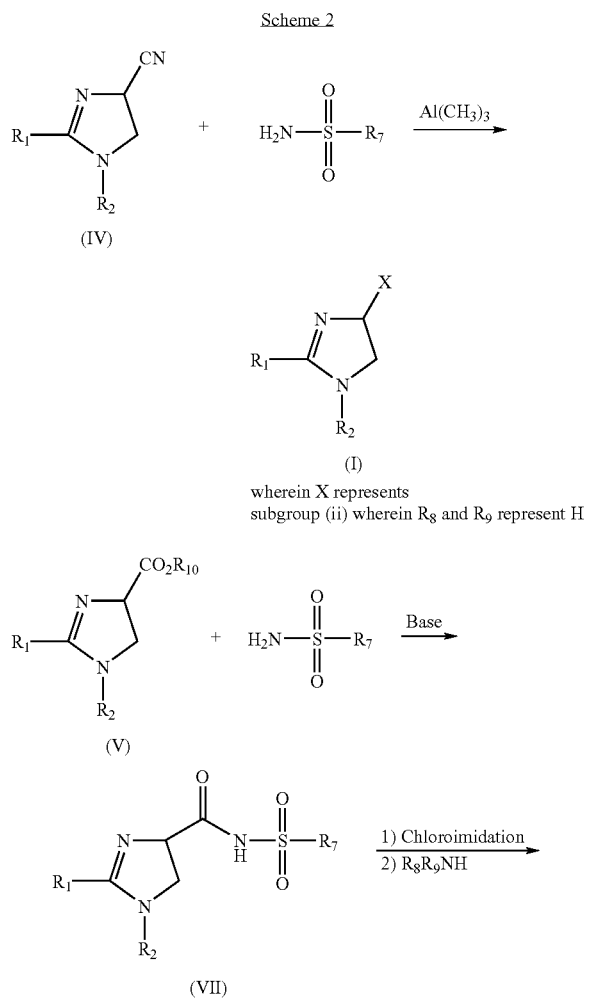

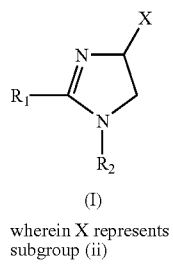

wherein X represents subgroup (ii)

The selection of the particular synthetic method depends on factors such as the compatibility of functional groups with the reagents used, the possibility to use protecting groups, catalysts, activating and coupling reagents and the ultimate structural features present in the final compound being prepared.

According to these procedures the following compounds can be prepared. They are intended to further illustrate the invention in more detail, and therefore are not deemed to restrict the scope of the invention in any way.

Pharmaceutical Preparations

The compounds of the invention can be brought into forms suitable for administration by means of usual processes using auxiliary substances such as liquid or solid carrier material. The pharmaceutical compositions of the invention may be administered enterally, orally, parenterally (intramuscularly or intravenously), rectally or locally (topically). They can be administered in the form of solutions, powders, tablets, capsules (including microcapsules), ointments (creams or gel) or suppositories. Suitable excipients for such formulations are the pharmaceutically customary liquid or solid fillers and extenders, solvents, emulsifiers, lubricants, flavorings, colorings and/or buffer substances. Frequently used auxiliary substances which may be mentioned are magnesium carbonate, titanium dioxide, lactose, mannitol and other sugars, talc, lactoprotein, gelatin, starch, cellulose and its derivatives, animal and vegetable oils such as fish liver oil, sunflower, groundnut or sesame oil, polyethylene glycol and solvents such as, for example, sterile water and mono- or polyhydric alcohols such as glycerol.

Compounds of the present invention are generally administered as pharmaceutical compositions which are important and novel embodiments of the invention because of the presence of the compounds, more particularly specific compounds disclosed herein. Types of pharmaceutical compositions that may be used include but are not limited to tablets, chewable tablets, capsules, solutions, parenteral solutions, suppositories, suspensions, and other types disclosed herein or apparent to a person skilled in the art from the specification and general knowledge in the art. In embodiments of the invention, a pharmaceutical pack or kit is provided comprising one or more containers filled with one or more of the ingredients of a pharmaceutical composition of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

Pharmacological Methods

In Vitro Affinity for Cannabinoid-$CB_1$ Receptors

The affinity of the compounds of the invention for cannabinoid $CB_1$ receptors can be determined using membrane preparations of Chinese hamster ovary (CHO) cells in which the human cannabinoid $CB_1$ receptor is stably transfected in conjunction with [$^3$H]CP-55,940 as radioligand. After incubation of a freshly prepared cell membrane preparation with the [$^3$H]-ligand, with or without addition of compounds of the invention, separation of bound and free ligand is performed by filtration over glassfiber filters. Radioactivity on the filter is measured by liquid scintillation counting.

In Vitro Cannabinoid-$CB_1$ Receptor Antagonism

In vitro $CB_1$ receptor antagonism can be assessed with the human $CB_1$ receptor cloned in Chinese hamster ovary (CHO) cells. CHO cells are grown in a Dulbecco's Modified Eagle's medium (DMEM) culture medium, supplemented with 10% heat-inactivated fetal calf serum. Medium is aspirated and replaced by DMEM, without fetal calf serum, but containing [$^3$H]-arachidonic acid and incubated overnight in a cell culture stove (5% $CO_2$/95% air; 37° C.; water-saturated atmosphere). During this period [$^3$H]-arachidonic acid is incorporated in membrane phospholipids. On the test day, medium is aspirated and cells are washed three times using 0.5 mL DMEM, containing 0.2% bovine serum albumin (BSA). Stimulation of the $CB_1$ receptor by WIN 55,212-2 leads to activation of $PLA_2$ followed by release of [$^3$H]-arachidonic acid into the medium. This WIN 55,212-2-induced release is concentration-dependently antagonized by $CB_1$ receptor antagonists.

In Vivo Cannabinoid-$CB_1$ Receptor Antagonism

In vivo $CB_1$ antagonism can be assessed with the CP-55,940-induced hypotension test in rat. Male normotensive rats (225–300 g; Harlan, Horst, The Netherlands) are anaesthetized with pentobarbital (80 mg/kg i.p.). Blood pressure is measured, via a cannula inserted into the left carotid artery, by means of a Spectramed DTX-plus pressure transducer (Spectramed B.V., Bilthoven, The Netherlands). After amplification by a Nihon Kohden Carrier Amplifier (Type AP-621G; Nihon Kohden B. V., Amsterdam, The Netherlands), the blood pressure signal is registered on a personal computer (Compaq Deskpro 386s), by means of a Po-Ne-Mah data-acquisition program (Po-Ne-Mah Inc., Storrs, USA). Heart rate is derived from the pulsatile pressure signal. All compounds are administered orally as a microsuspension in 1% methylcellulose 30 minutes before induction of the anesthesia which is 60 minutes prior to administration of the $CB_1$ receptor agonist CP-55,940. The injection volume is 10 ml/kg. After haemodynamic stabilization the $CB_1$ receptor agonist CP-55,940 (0.1 mg/kg i.v.) is administered and the hypotensive effect established. (Wagner, J. A.; Jarai, Z.; Batkai, S.; Kunos, G. Hemodynamic effects of cannabinoids: coronary and cerebral vasodilation mediated by cannabinoid $CB_1$ receptors. *Eur.J.Pharmacol.* 2001, 423, 203-10).

Pharmaceutically acceptable salts may be obtained using standard procedures well known in the art, for example by mixing a compound of the present invention with a suitable acid, for instance an inorganic acid such as hydrochloric acid, or with an organic acid.

Dose

The affinity of the compounds of the invention for cannabinoid receptors was determined as described above. From the binding affinity measured for a given compound of formula (1), one can estimate a theoretical lowest effective dose. At a concentration of the compound equal to twice the measured $K_i$-value, 100% of the cannabinoid receptors likely will be occupied by the compound. Converting that concentration to mg of compound per kg of patient yields a theoretical lowest effective dose, assuming ideal bioavailability. Pharmacokinetic, pharmacodynamic, and other considerations may alter the dose actually administered to a higher or lower value. The dosage expediently administered is 0.001–1000 mg/kg, preferably 0.1–100 mg/kg of patient's bodyweight.

EXAMPLE 1

Syntheses of Specific Compounds

Compounds 1–2

Part A: A magnetically stirred mixture of N-(4-chlorophenyl)-2,4-dichlorobenzenecarboxamidine (10.0 gram, 0.033 mol), 2-chloroacrylonitrile (5.7 gram, 0.065 mol) and N,N-diisopropylethylamine (DIPEA) (12.5 ml, 0.069 mol) in tetrahydrofuran (150 ml) is heated at reflux temperature for 40 hours ($N_2$ atmosphere). After cooling to room temperature the mixture is concentrated in vacuo. The residue is dissolved in a mixture of dichloromethane and water (200 ml/200 ml). The dichloromethane layer is collected, dried over $MgSO_4$, filtered and concentrated in vacuo. The residue is recrystallised from ethanol/water to give 1-(4-chlorophenyl)-2-(2,4-dichlorophenyl)-4,5-dihydro-1H-imidazole-4-carbonitrile (11.23 gram, 97% yield). $^1$H-NMR (400 MHz, $CDCl_3$): δ 4.28 (dd, J=10 and 8 Hz, 1H), 4.36 (t, J=10 Hz, 1H), 5.07 (dd, J=10 and 8 Hz, 1H), 6.68 (br d, J=8 Hz, 2H), 7.16 (br d, J=8 Hz, 2H), 7.32–7.36 (m, 2H), 7.45 (d, J=8 Hz, 1H).

Part B: Acetyl chloride (17.76 ml, 0.25 mol) is slowly added to ethanol (1 l) to give solution A. 1-(4-chlorophenyl)-2-(2,4-dichlorophenyl)-4,5-dihydro-1H-imidazole-4-carbonitrile (17.52 gram, 0.05 mol) is added in one portion to solution A. After cooling to room temperature the mixture is stirred for another 40 hours and concentrated in vacuo. The residue is dissolved in dichloromethane and washed (3×) with aqueous (5%) $NaHCO_3$. The dichloromethane layer is separated, dried over $MgSO_4$, filtered and concentrated in vacuo to give ethyl 1-(4-chlorophenyl)-2-(2,4-dichlorophenyl)-4,5-dihydro-1H-imidazole-4-carboxylate (18.0 gram, 90% yield) as a brown oil that slowly solidifies on standing. $^1$H-NMR (400 MHz, $CDCl_3$): δ 1.34 (t, J=7 Hz, 3H), 4.15 (dd, J=10 and 8 Hz, 1H), 4.22–4.41 (m, 3H), 4.91 (dd, J=10 and 8 Hz, 1H), 6.66 (br d, J=8 Hz, 2H), 7.11 (br d, J=8 Hz, 2H), 7.30 (dd, J=8 and 2 Hz, 1H), 7.33 (d, J=2 Hz, 1H), 7.46 (dd, J=8 Hz, 1H).

Part C: To a magnetically stirred solution of exo-2-aminobicyclo[2.2.1]heptane (0.67 ml, 0.009 mol) in anhydrous dichloromethane (10 ml) is added trimethylaluminum (5.4 ml of a 2N solution in hexane, 0.0108 mol) and the resulting solution is stirred for 20 minutes at room temperature. A solution of ethyl 1-(4-chlorophenyl)-2-(2,4-dichlorophenyl)-4,5-dihydro-1H-imidazole-4-carboxylate (2.385 g, 0.006 mol) in anhydrous dichloromethane (10 ml) is slowly added and the resulting mixture is reacted at 40° C. for 40 hours ($N_2$ atmosphere). After cooling to room temperature the mixture is quenched with aqueous (5%) $NaHCO_3$ and extracted with dichloromethane. The dichloromethane layer is separated, dried over $MgSO_4$, filtered and concentrated in vacuo to give a crude yellow syrup (2.58 gram) which is further purified with flash chromatography (silica gel, ethyl acetate/petroleum ether=8/2 (v/v)) to give the faster moving 1-(4-chlorophenyl)-2-(2,4-dichlorophenyl)-N-(exo-2-bicyclo[2.2.1]heptyl)-4,5-dihydro-1H-imidazole-4-carboxamide (dia-stereomer A) (0.70 gram, 25% yield) and the slower moving 1-(4-chlorophenyl)-2-(2,4-dichlorophenyl)—N—(exo-2-bicyclo[2.2.1]heptyl)-4,5-dihydro -1H-imidazole-4-carboxamide (diastereomer B) (0.69 gram, 25% yield).

Diastereomer A: $^1$H-NMR (400 MHz, CDCl$_3$): δ 1.10–1.58 (m, 7H), 1.76–1.84 (m, 1H), 2.26–2.30 (m, 2H), 3.74–3.82 (m, 1H), 4.27 (d, J~10 Hz, 2H), 4.78 (t, J~10 Hz, 1H), 6.65 (br d, J=8 Hz, 2H), 6.70–6.78 (m, 1H), 7.12 (br d, J=8 Hz, 2H), 7.29 (br s, 2H), 7.40 (br s, 1H).

Diastereomer B: $^1$H-NMR (400 MHz, CDCl$_3$): δ 1.10–1.56 (m, 7H), 1.78–1.85 (m, 1H), 2.17–2.20 (m, 1H), 2.26–2.30 (m, 1H), 3.76–3.82 (m, 1H), 4.25–4.30 (m, 2H), 4.78 (dd, J=10 and 8 Hz, 1H), 6.66 (br d, J=8 Hz, 2H), 6.80 (br d, J~7 Hz, 1H), 7.11 (br d, J=8 Hz, 2H), 7.30 (br s, 2H), 7.41 (br s, 1H.

boxylate (1.0 gram, ~0.0027 mol), benzotriazol-1-yloxytris (dimethylamino)phosphonium hexafluorophos-phate (BOP) (1.2 gram, 0.0027 mol), 1-aminopiperidine (0.3 gram, 0.003 mol) and triethylamine (1 ml) in DMF (30 ml) is stirred at room temperature for 16 hours. After concentration in vacuo, water is added and the resulting mixture is extracted (2×) with dichloromethane. The dichloromethane layers are collected, dried over MgSO$_4$, filtered and concentrated in vacuo to give a residue that is further purified by flash chromatography (silicagel, dichloromethane/methanol=95/5 (v/v)) to give 1-(4-chlorophenyl)-2-(2,4-dichlorophenyl)—N—(piperidin-1-yl)-4,5-dihydro-1H-imidazole-4-carboxamide (380 mg, 31% yield). Melting point: 113–116° C. $^1$H-NMR (200 MHz, CDCl$_3$): δ 1.33–1.48 (m, 2H), 1.60–1.80 (m, 4H), 2.68–2.82 (m, 4H), 4.28–4.35 (m, 2H), 4.84 (dd, J=11 and 9 Hz, 1H), 6.65 (br d, J=8 Hz, 2H), 7.11 (br d, J=8 Hz, 2H), 7.23–7.33 (m, 2H), 7.41 (d, J=2 Hz, 1H), 7.57 (br s, 1H).

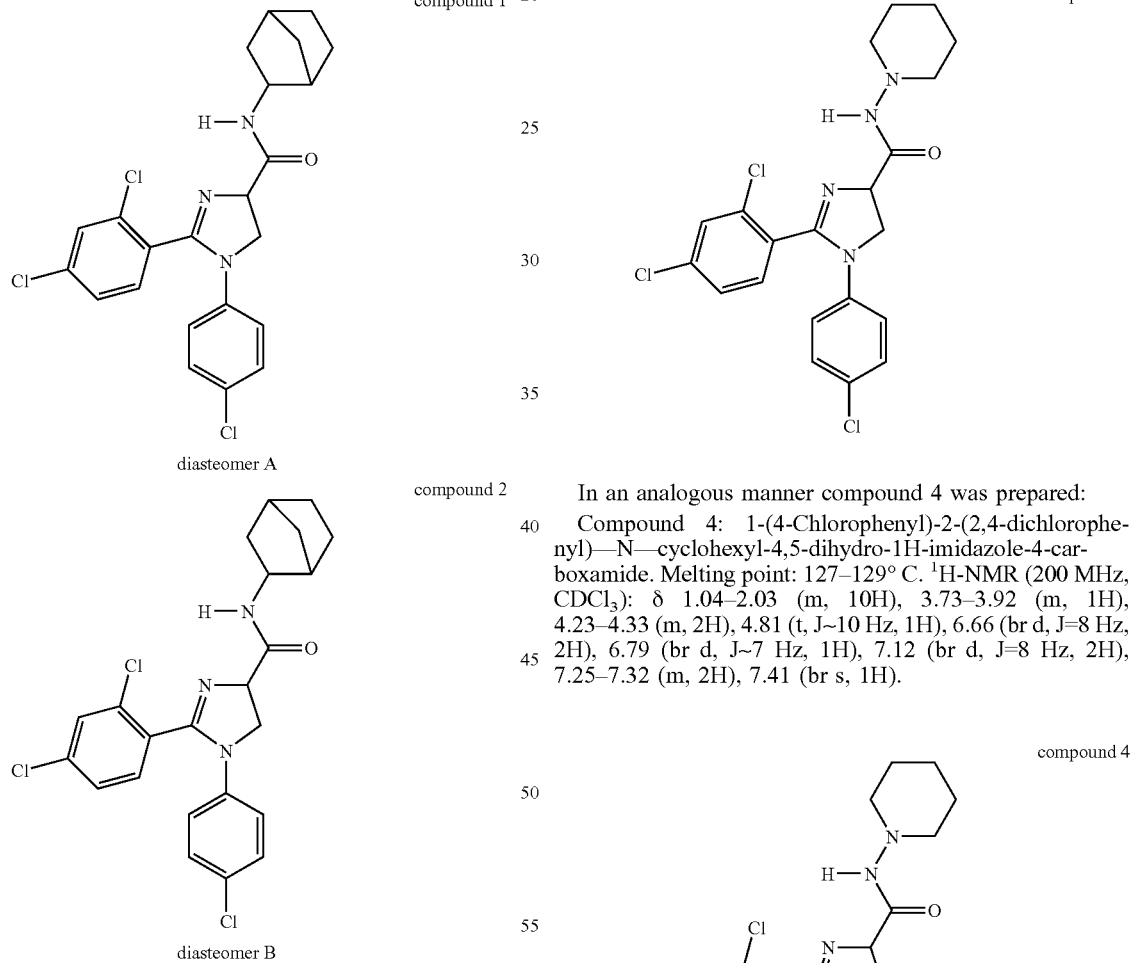

compound 1 diasteomer A compound 2 diasteomer B

Compounds 3 and 4

Part A: A mixture of ethyl 1-(4-chlorophenyl)-2-(2,4-dichlorophenyl)-4,5-dihydro-1H-imidazole-4-carboxylate (3.97 g, 0.01 mol) in methanol/water is reacted with LiOH (1.3 gram, 0.054 mol) at room temperature for 16 hours. The resulting mixture is concentrated in vacuo to give crude lithium 1-(4-chlorophenyl)-2-(2,4-dichlorophenyl)-4,5-dihydro-1H-imidazole-4-carboxylate (4.7 gram).

Part B: A mixture of the crude lithium 1-(4-chlorophenyl)-2-(2,4-dichlorophenyl)-4,5-dihydro-1H-imidazole-4-carcompound 3

In an analogous manner compound 4 was prepared:

Compound 4: 1-(4-Chlorophenyl)-2-(2,4-dichlorophenyl)—N—cyclohexyl-4,5-dihydro-1H-imidazole-4-carboxamide. Melting point: 127–129° C. $^1$H-NMR (200 MHz, CDCl$_3$): δ 1.04–2.03 (m, 10H), 3.73–3.92 (m, 1H), 4.23–4.33 (m, 2H), 4.81 (t, J~10 Hz, 1H), 6.66 (br d, J=8 Hz, 2H), 6.79 (br d, J~7 Hz, 1H), 7.12 (br d, J=8 Hz, 2H), 7.25–7.32 (m, 2H), 7.41 (br s, 1H).

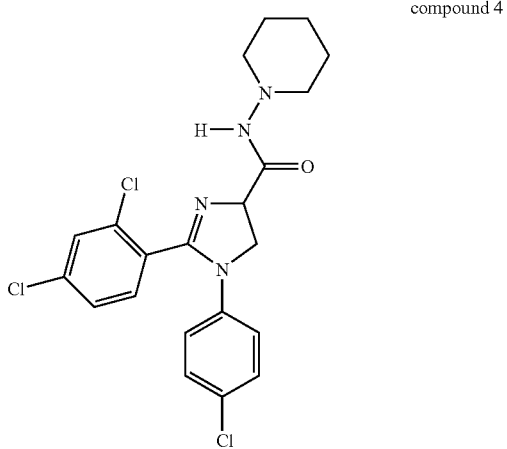

compound 4

Compounds 5–8

Part A: To a suspension of 4-chlorobenzenesulfonamide (0.45 gram, 0.00236 mol) in benzene (5 ml) is dropwise added trimethylaluminum (1.2 ml of a 2N solution in toluene, 0.0024 mol) to give a clear solution which is stirred at room temperature for 1 hour. 1-(4-Chlorophenyl)-2-(2,4-dichlorophenyl)-4,5-dihydro-1H-imidazole-4-carbonitrile (0.55 gram, 0.00157 mol) is added and the resulting mixture is heated at 90° C. for 16 hours. After cooling to room temperature a mixture of methanol/water (8/2 (v/v)) is slowly added, the solids are removed by filtration and washed with chloroform (50 ml). The filtrate is concentrated in vacuo. The residue is triturated with n-pentane and twice recrystallised from methanol to give 1-(4-chlorophenyl)-2-(2,4-dichlorophenyl)-N-[(4-chlorophenyl)sulfonyl]-4,5-dihydro-1H-imidazole-4-carboxamidine (0.435 gram, 51% yield). Melting point: 165–166° C. $^1$H-NMR (200 MHz, CDCl$_3$): δ 4.11–4.35 (m, 2H), 4.94 (dd, J=12 and 10 Hz, 1H), 6.63 (br d, J=8 Hz, 2H), 7.12 (br d, J=8 Hz, 2H), 7.22–7.52 (m, 6H), 7.90 (br d, J=8 Hz, 2H), 8.10–8.20 (m, 1H).

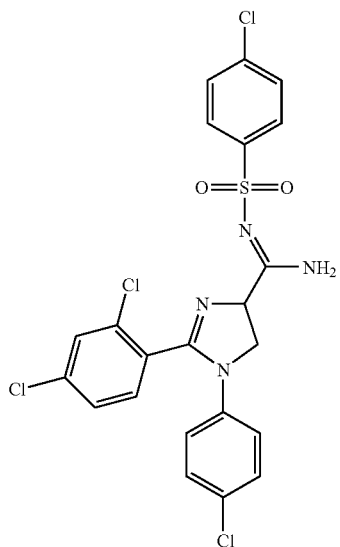

compound 5

In an analogous manner the compounds having formula (I) listed below have been prepared:

Compound 6: 1-(4-Chlorophenyl)-2-(2,4-dichlorophenyl)—N—[(4-fluorophenyl)-sulfonyl]-4,5-dihydro-1H-imidazole-4-carboxamidine. Melting point: 172–175° C. $^1$H-NMR (200 MHz, CDCl$_3$): δ 4.12–4.35 (m, 2H), 4.93 (dd, J=12 and 10 Hz, 1H), 6.63 (br d, J=8 Hz, 2H), 7.08–7.43 (m, 8H), 7.90–8.02 (m, 2H), 8.10–8.20 (m, 1H).

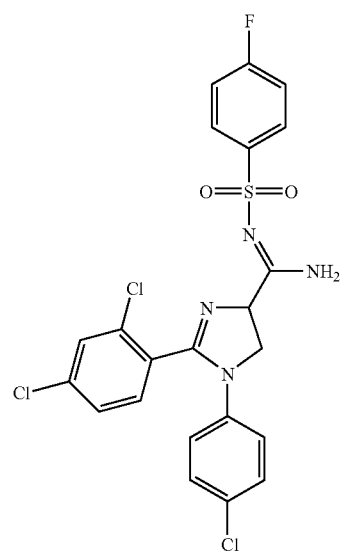

compound 6

Compound 7: 2-(4-Chlorophenyl)—N—(dimethylaminosulfonyl)-1-phenyl-4,5-dihydro-1H-imidazole-4-carboxamidine. Melting point: 136–139° C. $^1$H-NMR (200 MHz, CDCl$_3$): δ 2.79 (s, 6H), 4.20–4.40 (m, 2H), 4.97 (t, J~10 Hz, 1H), 6.83 (br d, J=8 Hz, 2H), 7.05–7.50 (m, 8H), 7.80–7.90 (m, 1H).

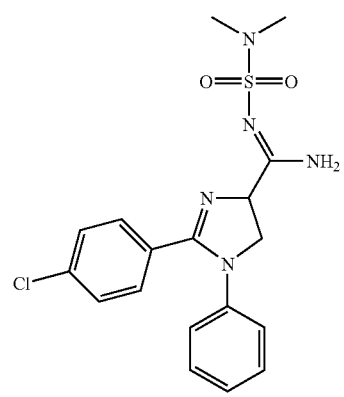

compound 7

Compound 8: 1-(4-chlorophenyl)-2-(2,4-dichlorophenyl)—N—(dimethylaminosul-fonyl)-4,5-dihydro-1H-imidazole-4-carboxamidine. Melting point: 146–147° C.

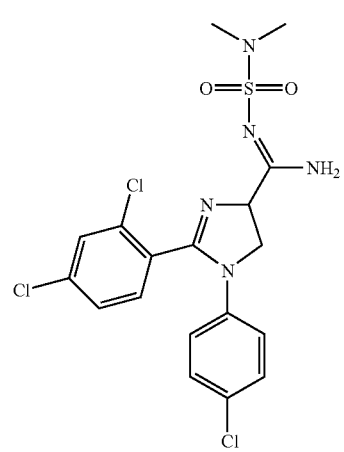

compound 8

EXAMPLE 2

Formulations As Used In Animal Studies

Formulation of Compound 1

For oral (p.o.) administration: to the desired quantity (0.5–15 mg) of the compound given above as 'Compound 1' in a glass tube, some glass beads were added and the substance was milled by vortexing for 2 minutes. After addition of 1 ml of a solution of 1% methylcellulose in water, the compound was suspended by vortexing for 10 minutes. For concentrations up and above 1 mg/ml remaining particles in the suspension were further suspended by using an ultrasonic bath.

EXAMPLE 3

Pharmacological Testresults

Cannabinoid receptor affinity and functional in vitro data data obtained according to the protocols given above are shown in the table below.

TABLE 1 pharmacological data

| | Human cannabinoid-$CB_1$ receptor | |
|---|---|---|
| Compound nr | In vitro affinity $pK_i$ value | In vitro antagonism $pA_2$-value (arachidonic acid release) |
| Compound 1 | 7.7 | — |
| Compound 2 | 7.0 | — |
| Compound 4 | 7.0 | 7.7 |
| Compound 8 | 6.8 | — |

The invention claimed is:

1. A compound of formula (I), or a tautomer thereof, a stereoisomers thereof, a prodrug thereof, or a salt of any of the foregoing:

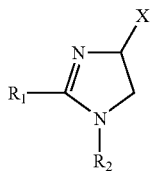

(I)

wherein:
  $R_1$ and $R_2$, each independently represent a phenyl, a thienyl, or a pyridyl group, which groups are optionally substituted with 1, 2, or 3 substituents Y, wherein said Y substituents, which may be the same or different, are each independently chosen from branched or linear $C_{1-3}$-alkyl, branched or linear $C_{1-3}$-alkoxy, phenyl, hydroxy, chloro, bromo, fluoro, iodo, trifluoromethyl, trifluoromethylthio, trifluoromethoxy, carboxyl, trifluoromethylsulfonyl, cyano, carbamoyl, sulfamoyl, and acetyl groups, or
  $R_1$ or $R_2$, or both $R_1$ and $R_2$, represent naphthyl;
  X represents a subgroup chosen from (i) and (ii),

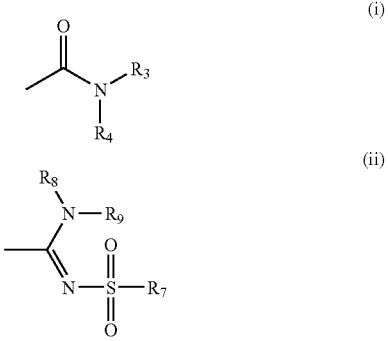

wherein:
  $R_3$ is chosen from a hydrogen atom and a branched or linear $C_{1-3}$ alkyl group;
  $R_4$ is chosen from:
    a branched or linear $C_{1-8}$-alkyl or $C_{3-8}$-cycloalkyl-$C_{1-2}$-alkyl, branched or linear $C_{1-8}$ alkoxy, $C_{3-8}$ cycloalkyl, $C_{5-10}$ bicycloalkyl, or $C_{6-10}$ tricycloalkyl group, which groups optionally contain one or more heteroatoms chosen from O, N, and S, and which groups are optionally substituted with a hydroxy group, 1–3 methyl groups, an ethyl group, or 1–3 fluoro atoms; or
    a phenoxy, benzyl, phenethyl or phenylpropyl group, which groups are each optionally substituted on their phenyl ring with 1–3 Y substituents, wherein each Y substituent may be the same or different, and is independently chosen from branched or linear $C_{1-3}$-alkyl, branched or linear $C_{1-3}$-alkoxy, phenyl, hydroxy, chloro, bromo, fluoro, iodo, trifluoromethyl, trifluoromethylthio, trifluoromethoxy, carboxyl, trifluoromethylsulfonyl, cyano, carbamoyl, sulfamoyl, and acetyl groups; or
    a pyridyl or thienyl group; and
    a group $NR_5R_6$, wherein:
      $R_5$ and $R_6$, together with the nitrogen atom to which they are attached, form a saturated or unsaturated, monocyclic or bicyclic, heterocyclic group having from 4 to 10 ring atoms, wherein said heterocyclic group contains one or two heteroatoms chosen from O, N, and S, and which group is optionally substituted with a branched or linear $C_{1-3}$ alkyl, a phenyl, a hydroxy or a trifluromethyl group or a fluoro atom; or
  $R_3$ and $R_4$, together with the nitrogen atom to which they are attached, form a saturated or unsaturated, monocyclic or bicyclic, heterocyclic group having from 4 to 10 ring atoms, which heterocyclic group contains one or two heteroatoms chosen from O, N, and S, and which group is optionally substituted with a branched or linear $C_{1-3}$ alkyl, a phenyl, an amino, a hydroxy or a trifluromethyl group, or a fluoro atom;
  $R_7$ represents a benzyl, phenyl, thienyl or pyridyl group, wherein the aromatic ring of said group is optionally substituted with 1, 2, 3 or 4 Y substituents, wherein each Y substituent may be the same or different, and is independently chosen from branched or linear $C_{1-3}$ alkyl, a branched or linear $C_{1-3}$ alkoxy, a phenyl, a hydroxy, a chloro, a bromo, a fluoro, an iodo, a trifluoromethyl, a trifluoromethylthio, a trifluoromethoxy, a carboxyl, a trifluoromethylsulfonyl, a cyano, a carbamoyl, a sulfamoyl, and an acetyl group; or $R_7$ represents a branched or linear $C_{1-8}$ alkyl, $C_{3-8}$ alkenyl, $C_{3-10}$ cycloalkyl, $C_{5-10}$ bicycloalkyl, $C_{6-10}$ tricycloalkyl, or a branched or linear $C_{5-8}$ cycloalkenyl; a naphthyl group, an amino group, a $C_{1-8}$ dialkylamino group, a $C_{1-8}$ monoalkylamino group, or a saturated or unsaturated, monocyclic or bicyclic, heterocyclic group having from 4 to 10 ring atoms, wherein said heterocyclic group contains 1 or 2 nitrogen atoms and optionally contains a heteroatom chosen from O and S, and is optionally substituted with a branched or linear $C_{1-3}$ alkyl, phyenyl, hydroxy or trifluoromethyl group or a fluro atom;

$R_8$ represents a hydrogen atom or a methyl group; and $R_9$ represents a hydrogen atom or a methyl, ethyl, or methoxy group.

2. A compound as claimed in claim 1, having the formula (I), or a tautomer thereof, a stereoisomer thereof, a prodrug thereof, or a salt of any of the foregoing:

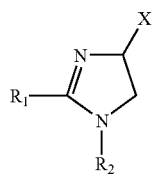

(I)

wherein:

$R_1$ and $R_2$ each independently represent a phenyl group that is optionally substituted with 1, 2, or 3 Y substituents, wherein each of said Y substituents may be the same or different, and is independently chosen from branched or linear $C_{1-3}$-alkyl, branched or linear alkoxy $C_{1-3}$-alkoxy, phenyl, hydroxy, chloro, bromo, fluoro, iodo, trifluoromethyl, trifluoromethylthio, trifluoromethoxy, carboxyl, trifluoromethylsulfonyl, cyano, carbamoyl, sulfamoyl, and acetyl groups; or $R_1$ or $R_2$, or both $R_1$ and $R_2$ independently represent a naphthyl, a thienyl, or a pyridyl group, X represents a subgroup chosen from (i) and (ii):

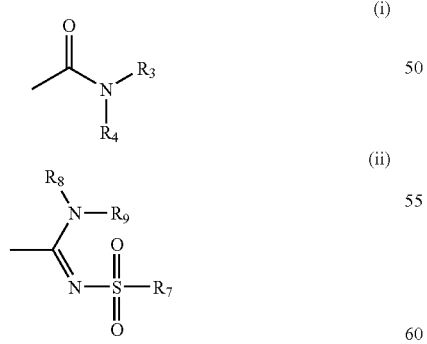

wherein:

$R_3$ represents a hydrogen atom;

$R_4$ is chosen from:

a branched or linear $C_{1-8}$ alkyl, or a branched or linear $C_{1-8}$ alkoxy or $C_{3-8}$ cycloalkyl group, which groups are optionally substituted with a hydroxy group, 1–3 methyl groups, an ethyl group, or 1–3 fluoro atoms; or $R_4$ represents a phenoxy, pyridyl, or thienyl group; or $R_4$ represents a group $NR_5R_6$, wherein:

$R_5$ and $R_6$, together with the nitrogen atom to which they are attached, form a saturated or unsaturated, monocyclic or bicyclic, heterocyclic group having from 4 to 10 ring atoms, wherein said heterocyclic group contains one or two heteroatoms chosen from O, N, and S; or $R_3$ and $R_4$, together with the nitrogen atom to which they are attached, form a saturated or unsaturated, monocyclic or bicyclic, heterocyclic group having from 4 to 10 ring atoms, which heterocyclic group contains one or two heteroatoms chosen from O, N, and S, and which group is optionally substituted with a methyl, hydroxy, or trifluoromethyl group, or a fluoro atom;

$R_7$ represents a phenyl group that is optionally substituted on its aromatic ring with 1, 2, 3, or 4 Y substituents, wherein each Y substituent may be the same or different, and is independently chosen from branched or linear $C_{1-3}$ alkyl, branched or linear $C_{1-3}$ alkoxy, phenyl, hydroxy, chloro, bromo, fluoro, iodo, trifluoromethyl, trifluoromethylthio, trifluoromethoxy, carboxyl, trifluoromethylsulfonyl, cyano, carbamoyl, sulfamoyl, and acetyl groups; or $R_7$ represents a branched or linear $C_{1-8}$ alkyl, a $C_{3-10}$ cycloalkyl, a $C_{5-10}$ bicyclo alkyl, a naphthyl, an amino group, a $C_{1-8}$ dialkylamino, a $C_{1-8}$ monoalkylamino or a saturated or unsaturated, monocyclic or bicyclic, heterocyclic group having from 4 to 10 ring atoms, which heterocyclic group contains 1 or 2 nitrogen atoms, and optionally comprises a heteroatom chosen from O and S, and which group is optionally substituted with a branched or linear $C_{1-3}$ alkyl or hydroxy group;

$R_8$ represents a hydrogen atom; and $R_9$ represents a hydrogen atom.

3. A compound of claim 1, wherein said compound is chosen from:

1-(4-chlorphenyl)-2-(2,4-dichlorophenyl)-N-(exo-2-bicyclo[2.2.1]heptyl)-4,5-dihydro-1H-imidazole-4-carboxamide (diastereomer A), 1-(4-chlorophenyl)-2-(2,4-dichlorophenyl)-N-(exo-2-bicyclo[2.2.1]heptyl)-4, 5-dihydro-1H-imidazole-4-carboxamide (diastereomer B), 1-(4-chlorophenyl)-2-(2,4-dichlorophenyl)-N-(piperidin-1-yl)-4,5-dihydro-1H-imidazole-4-carboxamide, 1-(4-chlorophenyl)-2-(2,4-dichlorophenyl)-N-cyclohexyl-4,5-dihydro-1H-imidazole-4-carboxamide, 1-(4-chlorophenyl)-2-(2,4-dichlorophenyl)-N-[(4-chlorophenyl)-sulfonyl]-4, 5-dihydro-1H-imidazole-4-carboxamidine, 1-(4-chlorophenyl)-2-(2,4-dichlorophenyl)-N-[(4-fluorophenyl)-sulfonyl]-4, 5-dihydro-1H-imidazole-4-carboxamidine, 2-(4-chlorophenyl)-N-(dimethylaminosulfonyl)-1-phenyl-4,5-dihydro-1H-imidazole-4-carboxamidine, and 1-(4-chlorophenyl)-2-(2,4-dichlorophenyl)-N-(dimethylaminosulfonyl)-4, 5-dihydro-1H-imidazole-4-carboxamidine.

4. A pharmaceutical composition comprising:

at least one pharmaceutically acceptable carrier and/or at least one pharmaceutically acceptable auxiliary substance; and a pharmaceutically effective amount of at least one compound of formula (I), or a tautomer thereof, a stereoisomer thereof, a prodrug thereof, or a salt of any of the foregoing:

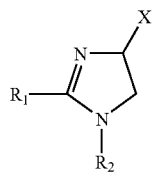
(I)

wherein:

$R_1$ and $R_2$, each independently represent a phenyl, a thienyl, or a pyridyl group, which groups are optionally substituted with 1, 2, or 3 substituents Y, wherein said Y substituents, which may be the same or different, are each independently chosen from branched or linear $C_{1-3}$-alkyl, branched or linear $C_{1-3}$-alkoxy, phenyl, hydroxy, chloro, bromo, fluoro, iodo, trifluoromethyl, trifluoromethylthio, trifluoromethoxy, carboxyl, trifluoromethylsulfonyl, cyano, carbamoyl, sulfamoyl, and acetyl groups, or $R_1$ or $R_2$, or both $R_1$ and $R_2$, represent naphthyl;

X represents a subgroup chosen from (i) and (ii),

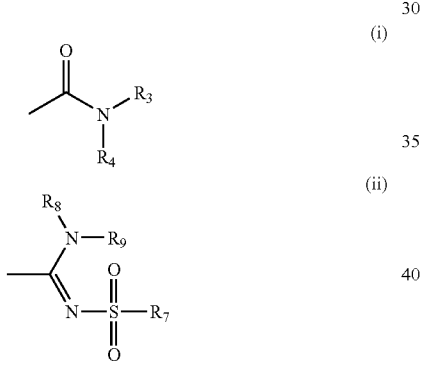

wherein:

$R_3$ is chosen from a hydrogen atom and a branched or linear $C_{1-3}$ alkyl group;

$R_4$ is chosen from:
  a branched or linear $C_{1-8}$-alkyl or $C_{3-8}$-cycloalkyl-$C_{1-2}$-alkyl, branched or linear $C_{1-8}$ alkoxy, $C_{3-8}$ cycloalkyl, $C_{5-10}$ bicycloalkyl, or $C_{6-10}$ tricycloalkyl group, which groups optionally contain one or more heteroatoms chosen from O, N, and S, and which groups are optionally substituted with a hydroxy group, 1–3 methyl groups, an ethyl group, or 1–3 fluoro atoms; or
  a phenoxy, benzyl, phenethyl or phenyipropyl group, which groups are each optionally substituted on their phenyl ring with 1–3 Y substituents, wherein each Y substituent may be the same or different, and is independently chosen from branched or linear $C_{1-3}$-alkyl, branched or linear $C_{1-3}$-alkoxy, phenyl, hydroxy, chloro, bromo, fluoro, iodo, trifluoromethyl, trifluoromethylthio, trifluoromethoxy, carboxyl, trifluoromethylsulfonyl, cyano, carbamoyl, sulfamoyl, and acetyl groups; or a pyridyl or thienyl group; and a group $NR_5R_6$, wherein:
  $R_5$ and $R_6$, together with the nitrogen atom to which they are attached, form a saturated or unsaturated, monocyclic or bicyclic, heterocyclic group having from 4 to 10 ring atoms, wherein said heterocyclic group contains one or two heteroatoms chosen from O, N, and S, and which group is optionally substituted with a branched or linear $C_{1-3}$ alkyl, a phenyl, a hydroxy or a trifluromethyl group or a fluoro atom; or $R_3$ and $R_4$, together with the nitrogen atom to which they are attached, form a saturated or unsaturated, monocyclic or bicyclic, heterocyclic group having from 4 to 10 ring atoms, which heterocyclic group contains one or two heteroatoms chosen from O, N, and S, and which group is optionally substituted with a branched or linear $C_{1-3}$ alkyl, a phenyl, a amino, a hydroxy or a triflurommethyl group, or a fluoro atom;

$R_7$ represents a benzyl, phenyl, thienyl or pyridyl group, wherein the aromatic ring of said group is optionally substituted with 1, 2, 3 or 4 Y substituents, wherein each Y substituent may be the same or different, and is independently chosen from branched or linear $C_{1-3}$ alkyl, a branched or linear $C_{1-3}$ alkoxy, a phenyl, a hydroxy, a chloro, a bromo, a fluoro, an iodo, a trifluoromethyl, a trifluoromethylthio, a trifluoromethoxy, a carboxyl, a trifluoromethylsulfonyl, a cyano, a carbamoyl, a sulfamoyl, and an acetyl group; or $R_7$ represents a branched or linear $C_{1-8}$ alkyl, $C_{3-8}$ alkenyl, $C_{3-10}$ cycloalkyl, $C_{5-10}$ bicycloalkyl, $C_{6-10}$ tricycloalkyl, or a branched or linear $C_{5-8}$ cycloalkenyl; a naphthyl group, an amino group, a $C_{1-8}$ dialkylamino group, a $C_{1-8}$ monoalkylamino group, or a saturated or unsaturated, monocyclic or bicyclic, heterocyclic group having from 4 to 10 ring atoms, wherein said heterocyclic group contains 1 or 2 nitrogen atoms and optionally contains a heteroatom chosen from O and S, and is optionally substituted with a branched or linear $C_{1-3}$ alkyl, phyenyl, hydroxy or trifluoromethyl group or a fluro atom;

$R_8$ represents a hydrogen atom or a methyl group; and $R_9$ represents a hydrogen atom or a methyl, ethyl, or methoxy group.

5. The pharmaceutical composition of claim 4, wherein said pharmaceutical composition further comprises at least one lipase inhibitor.

6. The pharmaceutical composition of claim 5, wherein said at least one lipase inhibitor is chosen from orlistat and lipstatin.

7. A method for preparing a pharmaceutical composition comprising: mixing a pharmaceutically effective amount of at least one compound of formula (I), or a tautomer thereof, a stereoisomer thereof, a prodrug thereof, or a salt of any of the foregoing:

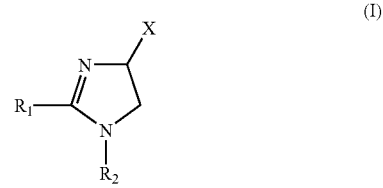
(I)

wherein:
R₁ and R₂, each independently represent a phenyl, a thienyl, or a pyridyl group, which groups are optionally substituted with 1, 2, or 3 substituents Y, wherein said Y substituents, which may be the same or different, are each independently chosen from branched or linear $C_{1-3}$-alkyl, branched or linear $C_{1-3}$-alkoxy, phenyl, hydroxy, chloro, bromo, fluoro, iodo, trifluoromethyl, trifluoromethylthio, trifluoromethoxy, carboxyl, trifluoromethylsulfonyl, cyano, carbamoyl, sulfamoyl, and acetyl groups, or R₁ or R₂, or both R₁ and R₂, represent naphthyl;

X represents a subgroup chosen from (i) and (ii),

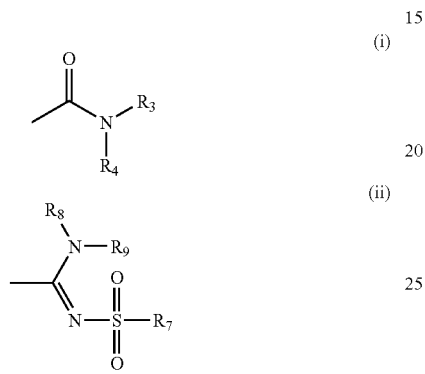

wherein:
R₃ is chosen from a hydrogen atom and a branched or linear $C_{1-3}$ alkyl group;

R₄ is chosen from:
a branched or linear $C_{1-8}$-alkyl or $C_{3-8}$-cycloalkyl-$C_{1-2}$-alkyl, branched or linear $C_{1-8}$ alkoxy, $C_{3-8}$ cycloalkyl, $C_{5-10}$ bicycloalkyl, or $C_{6-10}$ tricycloalkyl group, which groups optionally contain one or more heteroatoms chosen from O, N, and S, and which groups are optionally substituted with a hydroxy group, 1–3 methyl groups, an ethyl group, or 1–3 fluoro atoms; or a phenoxy, benzyl, phenethyl or phenylpropyl group, which groups are each optionally substituted on their phenyl ring with 1–3 Y substituents, wherein each Y substituent may be the same or different, and is independently chosen from branched or linear $C_{1-3}$-alkyl, branched or linear $C_{1-3}$-alkoxy, phenyl, hydroxy, chloro, bromo, fluoro, iodo, trifluoromethyl, trifluoromethylthio, trifluoromethoxy, carboxyl, trifluoromethylsulfonyl, cyano, carbamoyl, sulfamoyl, and acetyl groups; or a pyridyl or thienyl group; and a group NR₅R₆, wherein:

R₅ and R₆, together with the nitrogen atom to which they are attached, form a saturated or unsaturated, monocyclic or bicyclic, heterocyclic group having from 4 to 10 ring atoms, wherein said heterocyclic group contains one or two heteroatoms chosen from O, N, and S, and which group is optionally substituted with a branched or linear $C_{1-3}$ alkyl, a phenyl, a hydroxy or a trifluromethyl group or a fluoro atom; or R₃ and R₄, together with the nitrogen atom to which they are attached, form a saturated or unsaturated, monocyclic or bicyclic, heterocyclic group having from 4 to 10 ring atoms, which heterocyclic group contains one or two heteroatoms chosen from O, N, and S, and which group is optionally substituted with a branched or linear $C_{1-3}$ alkyl, a phenyl, a amino, a hydroxy or a trifluromethyl group, or a fluoro atom;

R₇ represents a benzyl, phenyl, thienyl or pyridyl group, wherein the aromatic ring of said group is optionally substituted with 1, 2, 3 or 4 Y substituents, wherein each Y substituent may be the same or different, and is independently chosen from branched or linear $C_{1-3}$ alkyl, a branched or linear $C_{1-3}$ alkoxy, a phenyl, a hydroxy, a chloro, a bromo, a fluoro, an iodo, a trifluoromethyl, a trifluoromethylthio, a trifluoromethoxy, a carboxyl, a trifluoromethylsulfonyl, a cyano, a carbamoyl, a sulfamoyl, and an acetyl group; or R₇ represents a branched or linear $C_{1-8}$ alkyl, $C_{3-8}$ alkenyl, $C_{3-10}$ cycloalkyl, $C_{5-10}$ bicycloalkyl, $C_{6-10}$ tricycloalkyl, or a branched or linear $C_{5-8}$ cycloalkenyl; a naphthyl group, an amino group, a $C_{1-8}$ dialkylamino group, a $C_{1-8}$ monoalkylamino group, or a saturated or unsaturated, monocyclic or bicyclic, heterocyclic group having from 4 to 10 ring atoms, wherein said heterocyclic group contains 1 or 2 nitrogen atoms and optionally contains a heteroatom chosen from O and S, and is optionally substituted with a branched or linear $C_{1-3}$ alkyl, phyenyl, hydroxy or trifluoromethyl group or a fluro atom;

R₈ represents a hydrogen atom or a methyl group; and

R₉ represents a hydrogen atom or a methyl, ethyl, or methoxy group, with at least one pharmaceutically acceptable carrier, at least one pharmaceutically acceptable auxiliary substance, or a combination thereof.

* * * * *